United States Patent
Lee et al.

(10) Patent No.: US 11,026,987 B2
(45) Date of Patent: Jun. 8, 2021

(54) COMPOSITION FOR REMEDYING FEMALE CLIMACTERIC SYNDROME SYMPTOMS

(71) Applicant: LG Household & Health Care Ltd., Seoul (KR)

(72) Inventors: Bo-Young Lee, Daejeon (KR); Ho-Song Cho, Daejeon (KR); Soon-Ran Song, Daejeon (KR); Won-Kyung Lee, Daejeon (KR); Jeong-Hoon Jeon, Daejeon (KR); Chang-Il Choi, Daejeon (KR); Sang-Hwa Lee, Daejeon (KR)

(73) Assignee: LG Household & Health Care Ltd.

( * ) Notice: Subject to any disclaimer, the term of this patent is extended or adjusted under 35 U.S.C. 154(b) by 0 days.

(21) Appl. No.: 16/491,759

(22) PCT Filed: Jul. 19, 2017

(86) PCT No.: PCT/KR2017/007793
§ 371 (c)(1),
(2) Date: Sep. 6, 2019

(87) PCT Pub. No.: WO2018/164325
PCT Pub. Date: Sep. 13, 2018

(65) Prior Publication Data
US 2020/0261526 A1    Aug. 20, 2020

(30) Foreign Application Priority Data
Mar. 7, 2017   (KR) .................. 10-2017-0029014

(51) Int. Cl.
*A61K 36/488*   (2006.01)
*A61K 36/48*    (2006.01)

(52) U.S. Cl.
CPC ........ *A61K 36/48* (2013.01); *A61K 2236/333* (2013.01)

(58) Field of Classification Search
CPC .................................................. A61K 36/488
See application file for complete search history.

(56) References Cited

FOREIGN PATENT DOCUMENTS

| CN | 101518563 A | 9/2009 |
| CN | 101543526 A | 9/2009 |

(Continued)

OTHER PUBLICATIONS

Kamiya et al., "Evaluation of the estrogenic activity of Pueraria (kudzu) flower extract and its major isoflavones using ER-binding and uterotrophic bioassays," Pharmacology & Pharmacy 4:255-260, 2013.*

(Continued)

*Primary Examiner* — Rosanne Kosson
(74) *Attorney, Agent, or Firm* — Lerner, David, Littenberg, Krumholz & Mentlik, LLP

(57) ABSTRACT

The present disclosure relates to a composition for preventing, treating or remedying female climacteric syndrome symptoms, which contains an extract of *Pueraria thomsonii* flower or bud. The composition according to the present disclosure shows quick effects for preventing, remedying and/or treating female climacteric syndrome symptoms, particularly facial flushing and/or osteoporosis, and thus can be utilized for the hormone replacement therapy (HRT) used for preventing or remedying climacteric syndrome symptoms.

6 Claims, 3 Drawing Sheets

(56) References Cited

FOREIGN PATENT DOCUMENTS

| CN | 103784497 A | 5/2014 |
|---|---|---|
| JP | 2000302667 A | 10/2000 |

OTHER PUBLICATIONS

Melissa Conrad Stöppler, The Stages of Menopause, Women's Health, On Health, https://www.onhealth.com/content/1/menopause_women_aging, Aug. 2016.*

International Search Report for Application No. PCT/KR2017/007793 dated Dec. 4, 2017, pp. 1-8.

Lim, D.W. et al., "Effects of Dietary Isoflavones from Puerariae Radix on Lipid and Bone Metabolism in Ovariectomized Rats", Nutrients, Jul. 17, 2013, vol. 5, pp. 2734-2746.

Jiang, R.-W. et al., "A Comparative Study on Aqueous Root Extracts of pueraria Thomsonii and Pueraria Lobata by Antioxidant Assay and HPLC Fingerprint Analysis", Journal of Ethnopharmacology, 2005, vol. 96, pp. 133-138.

Kamiya, T. et al., "The Isoflavone-rich Fraction of the Crude Extract of the Puerariae Flower Increases Oxygen Consumption and BAT UCP1 Expression in High-fat Diet-Fed Mice", Global Journal of Health Science, Aug. 12, 2012, vol. 4, No. 5, pp. 147-155.

Miadokova, E., "Isoflavonoids—An Overview of Their Biological Activities and Potential Health Benefits", Interdisciplinary Toxicology, Nov. 2009, vol. 2, No. 4, pp. 211-218.

Cho, H. et al., "The Effects of Pueraria Thomsonii Flower Extract on Estrogenic Activity, Osteoblast Differentiation and Osteoclast Formation in Vitro", Maturitas, Jun. 2017, vol. 100, p. 189, thesis No. P135.

Chinese Search Report for Application No. CN2017800879114 dated Mar. 23, 2021.

Peng et al., Effects of Daidzeinon Proliferaaaation and Differentiaion of Cultured Rat Osteoblast in Vitro, vol. 8, No. 4, Aug. 2007, English Abstract Only.

* cited by examiner

COMPOSITION FOR REMEDYING FEMALE CLIMACTERIC SYNDROME SYMPTOMS

CROSS-REFERENCE TO RELATED APPLICATIONS

The present application is a national phase entry under 35 U.S.C. § 371 of International Application No. PCT/KR2017/007793 filed Jul. 19, 2017, which claims priority from Korean Patent Application No. 10-2017-0029014 filed Mar. 7, 2017, all of which are incorporated herein by reference.

TECHNICAL FIELD

The present disclosure relates to a composition for preventing, remedying and/or treating female climacteric syndrome symptoms, more particularly to a composition which is particularly effective in preventing, remedying and/or treating facial flushing and/or osteoporosis among the female climacteric syndrome symptoms. The present disclosure also relates to a method for preventing, remedying and/or treating climacteric syndrome symptoms, more particularly to a method for preventing, remedying and/or treating facial flushing, and/or osteoporosis among the female climacteric syndrome symptoms.

BACKGROUND ART

Women's climacteric (menopause) refers to the stopping of menstruation occurring around 50 years of age as the ovaries stop functioning. It means the loss of reproductive capability and is a physiological change rather than a pathological phenomenon. At present, the average life span of Korean women is 81.2 years (National Statistical Office, 2011). Suppose that the average age when the menopause occurs in Korean women is 50 years as reported by the Korean Society for Obstetrics and Gynecology, they live more than about ⅓ of their lives with depleted female hormone (Sung-Chul Kim, Korea Pharmaceutical Information Center).

With the menopause, women experience changes throughout the body including the blood vascular system, musculoskeletal system, genitourinary system, cranial nerves, etc. due to the imbalance and decrease of female hormone secretion. That is to say, they experience vasomotor symptoms and psychological symptoms such as facial flushing, night sweating, sleep disorder, fatigue, depression, anxiety, attention deficit and memory impairment, sexual pain due to the contraction of the genitourinary system, oliguria, loss of skin elasticity due to decreased collagen, skin elasticity, and various diseases such as dementia, etc. (non-patent document 1). Although there are differences among individuals, it is reported that the quality of life of women worsen as they experience more and severer climacteric syndrome symptoms (non-patent document 2). In addition, it is highly likely that the climacteric syndrome symptoms will develop into chronic diseases with physical aging.

Hormone therapy, drug therapy, exercise therapy or diet may be used for treatment of the climacteric syndrome symptoms. However, the most frequently used female hormone therapy can increase the risk of breast cancer, etc. and a long-term use can increase the occurrence of uterine cancer, thrombotic vascular diseases, gallbladder diseases and hypertension. Therefore, a lot of researches are being carried out recently on phytoestrogens which are reported to have similar functions as estrogen in order to replace the estrogen therapy and other drug therapies (non-patent document 3).

DISCLOSURE

Technical Problem

The present disclosure is designed to solve the problems of the related art, and therefore the present disclosure is directed to providing a composition for treating, preventing or remedying female climacteric syndrome symptoms.

In particular, the present disclosure is directed to providing a composition which has an excellent effect in preventing, remedying or treating sweating, facial flushing and/or osteoporosis among the female climacteric syndrome symptoms.

The present disclosure is also directed to providing a method for treating, preventing or remedying female climacteric syndrome symptoms.

In particular, the present disclosure is directed to providing an excellent method for preventing, remedying or treating sweating, facial flushing and/or osteoporosis among the female climacteric syndrome symptoms.

Technical Solution

An aspect of the present disclosure provides use of a *Pueraria thomsonii* extract for preparing a composition for treating, preventing or remedying female climacteric syndrome symptoms, sweating, facial flushing and/or osteoporosis.

Specifically, the composition may be contained in a functional food composition or a pharmaceutical composition.

The present disclosure provides a method for treating or remedying climacteric syndrome symptoms by administering a *Pueraria thomsonii* extract to a patient in need of treatment of female climacteric syndrome symptoms. The present disclosure also provides a method for preventing climacteric syndrome symptoms by administering a *Pueraria thomsonii* extract to a subject in need of prevention of female climacteric syndrome symptoms.

The present disclosure provides a composition for preventing or remedying female climacteric syndrome symptoms, which contains a *Pueraria thomsonii* extract as an active ingredient.

More specifically, the present disclosure provides a composition for preventing or remedying female climacteric syndrome symptoms, which contains an extract of *Pueraria thomsonii* flower or bud as an active ingredient.

The extract of *Pueraria thomsonii* flower or bud according to the present disclosure can provide superior effects of preventing or remedying sweating, facial flushing and osteoporosis as compared to other parts.

Unless specified otherwise, the *Pueraria thomsonii* mentioned in the present specification may be understood to refer to the extract of *Pueraria thomsonii* flower or bud.

Another aspect of the present disclosure provides a composition for treating, preventing or remedying sweating or facial flushing which contains a *Pueraria thomsonii* flower or bud extract as an active ingredient. The present disclosure provides a method for treating or remedying sweating and/or facial flushing by administering a *Pueraria thomsonii* extract to a patient in need of treatment of the symptoms. Also, the present disclosure provides a method for preventing sweating and/or facial flushing by administering a *Pueraria thomsonii* extract to a subject in need of treatment of the symptoms.

Specifically, the *Pueraria thomsonii* extract may be obtained by extracting *Pueraria thomsonii* flower or bud with 60-90% ethanol.

Another aspect of the present disclosure provides a composition for treating, preventing or remedying osteoporosis which contains a *Pueraria thomsonii* flower or bud extract as an active ingredient.

The present disclosure provides a method for treating or remedying osteoporosis by administering a *Pueraria thomsonii* extract to a patient in need of treatment of osteoporosis. Also, the present disclosure provides a method for preventing osteoporosis by administering a *Pueraria thomsonii* extract to a subject in need of treatment of the symptom.

Specifically, the composition may be obtained by extracting *Pueraria thomsonii* flower or bud with 60-90% ethanol.

The *Pueraria thomsonii* is a plant known as kudzu in Korea. It has not been studied a lot as comparted to other plants in the genus *Pueraria*.

The inventors of the present disclosure have researched on methods for preventing or remedying female climacteric syndrome symptoms for a long period of time. As a result, they have identified that the *Pueraria thomsonii* extract which has not been studied a lot has an effect of relieving climacteric syndrome symptoms and have completed the present disclosure.

The inventors of the present disclosure have identified that the *Pueraria thomsonii* extract has superior effect of relieving climacteric syndrome symptoms as compared to plants in the genus *Pueraria*.

The extract of *Pueraria thomsonii* flower or bud can provide excellent effect of treating, remedying or preventing women's climacteric diseases through a combination of the ingredients contained therein. In particular, excellent effect of treating, remedying or preventing sweating or facial flushing can be expected.

In the present disclosure, the 'climacteric syndrome symptoms' collectively refer to the symptoms and diseases occurring women around the menopause due to decreased secretion of estrogen because of aging of the ovaries, etc. They are also called 'climacteric syndromes' or 'postmenopausal symptoms'. The climacteric or postmenopausal symptoms include, for example, facial flushing, sweating, nervousness, depression, dizziness, fatigue, arthralgia, muscular pain, headache, palpitation, crawling sensation, sweating during sleep, sleep disorder, skin dryness, vaginal dryness, vaginal atrophy, lower urinary tract contraction, sexual pain, vaginitis, cystitis, dysuria, urinary urgency, attention deficit, memory impairment, anxiety, oversensitiveness, memory decline, osteoporosis, etc., although not being limited thereto.

In the present disclosure, the 'facial flushing' is the representative vasomotor symptom known to be experienced by 75% of postmenopausal women and refers to abrupt reddening of the face, neck and chest accompanied by unpleasant flushing and sweating. The climacteric vasomotor symptom occurs as the thermoneutral zone in the hypothalamus becomes narrow due to the climacteric change of hormones and hot flush is felt if the body temperature is increased only slightly.

In the present disclosure, the 'sweating' refers to secretion of sweat from the sweat glands of the skin. It is the symptom of abrupt perspiration accompanied by generation of heat.

In the present disclosure, the 'osteoporosis' refers to the state of increased risk of bone fracture due to decreased bone strength. It is caused by genetic factors, early menopause, medication, smoking, etc. Accordingly, 'climacteric osteoporosis' may be caused in women by decreased hormone production due to menopause, etc. The climacteric osteoporosis refers to the osteoporotic symptom occurring in post-menstrual women due to the imbalance of osteoblasts involved in bone formation and osteoclasts involved in bone tissue breakdown and resorption because of decreased hormone production.

In the present disclosure, 'prevention' refers to any action of inhibiting or delaying a symptom by administering the composition of the present disclosure.

In the present disclosure, 'treatment' refers to any action of improving or remedying a symptom by administering the composition of the present disclosure.

In the present disclosure, 'remedying' refers to any action of improving or favorably changing a symptom as compared to before administration by administering the composition of the present disclosure.

The extract may be contained in the composition of the present disclosure in an effective amount. The term 'effective amount' refers to the amount of the extract capable of inhibiting or delaying climacteric syndrome symptoms, particularly sweating, facial flushing or osteoporosis, or capable of improving the existing symptoms.

The content of the *Pueraria thomsonii* extract contained in the composition is not particularly limited and can vary as long as the climacteric syndrome symptoms, or sweating, facial flushing or osteoporosis can be prevented, remedied or treated. For example, the *Pueraria thomsonii* extract may be contained in an amount of 0.001-50 wt % based on the total composition.

Also, in an exemplary embodiment of the present disclosure, the composition may contain the extract in an amount of 1-1000 mg, specifically 5-500 mg, based on 1 g of the composition.

The term 'flower' used in this specification refers to the reproductive organ of an angiosperm, consisting of a pistil, stamens, petals and calyx. The flower in 'bud' state which has not blossomed yet is also included in the scope of the flower in the present disclosure.

In the present disclosure, the 'extract' may be prepared by extracting a plant with an extraction solvent, or by fractionating the extract obtained by extracting with an extraction solvent by adding a fractionation solvent.

The extract or fraction includes the extract itself and any form of extract that can be prepared using the extract, such as a diluent or condensate of the extract, a dried product obtained by drying the extract, a crude purification product, a purification product or a mixture of the extract, etc. Specifically, the extract of the present disclosure may be used after being prepared into dried powder. Also, after an extraction or fractionation process has been conducted, the solvent may be removed by filtration under reduced pressure or additional concentration and/or lyophilization. The obtained extract may be stored in a deep freezer until use.

The extraction solvent is not particularly limited and any solvent known in the art may be used as long as the extract having the effect desired by the present disclosure can be obtained. Specifically, one or more selected from a group consisting of water and an organic solvent may be used. The organic solvent may be one or more solvent selected from a group consisting of a $C_{1-5}$ alcohol such as methanol, ethanol, etc., ethyl acetate, acetone and chloroform.

Specifically, ethanol may be used. The ethanol may be specifically 35-95% ethanol, more specifically 60-90% ethanol.

In a specific example, the effect of remedying climacteric syndrome symptoms was investigated using a *Pueraria thomsonii* extract extracted using 85% ethanol. As a result, it was confirmed that the activity of estrogen receptors was improved in cells treated with the extract, and the climacteric syndrome symptoms were remedied in a human test group who taken in the extract.

The fractionation solvent may be water, butanol, ethyl acetate, chloroform, hexane or a mixture thereof. The fraction may be a fraction obtained by performing a fractionation process for an extract, specifically a crude extract, prepared by the extraction method described above. The fractionation solvent may be a solvent selected from a group consisting of ethyl acetate, ether, chloroform, benzene, hexane, methylene chloride and a mixture solvent thereof. Specifically, it may be hexane. Specifically, the fractionation process may be performed by sequentially adding hexane, chloroform, ethyl acetate, butanol and water to the crude extract and then sequentially obtaining phase-separated hexane, chloroform, ethyl acetate, butanol and water fractions.

In the present disclosure, the method for preparing the extract is not specially limited and the method commonly used in the art may be used. As non-limiting examples of the extraction method, hot water extraction, ultrasonic extraction, filtration, reflux extraction, etc. may be performed either alone or in combination. Also, the extraction may be performed more than once in order to obtain a high-purity extract.

The present disclosure may provide a cosmetic composition, a pharmaceutical composition or a food composition for preventing or remedying female climacteric syndrome symptoms, which contains a *Pueraria thomsonii* extract as an active ingredient.

The composition may be provided in the form of cosmetics, medicine, food or quasi-drugs.

The pharmaceutical composition according to the present disclosure may contain a pharmaceutically effective amount of a *Pueraria thomsonii* extract alone or may further contain one or more pharmaceutically acceptable carrier, excipient or diluent. The term "pharmaceutically acceptable" means that the composition is a nontoxic composition which is physiologically acceptable and usually does not cause gastroenteric trouble, allergic reactions such as dizziness or other similar reactions when administered to human, without inhibiting the action of the active ingredient.

Examples of the carrier, excipient or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, mineral oil, etc. Also, the pharmaceutical composition may further contain a filler, an anti-agglomerant, a lubricant, a wetting agent, a flavor, an emulsifier, an antiseptic, etc.

The "pharmaceutically effective amount" means an amount exhibiting a better reaction as compared to a negative control group, specifically an amount effective for exhibiting an effect of preventing, remedying and/or treating climacteric disorder.

Also, the pharmaceutical composition of the present disclosure may be formulated using a method known in the art so as to provide quick, sustained or delayed release of the active ingredient after administration to a mammal. The formulation may be in the form of a powder, a granule, a tablet, an emulsion, a syrup, an aerosol, a soft or hard gelatin capsule, a sterile solution for injection, or a sterile powder.

The pharmaceutical composition of the present disclosure may be administered orally or parenterally although the administration route is not limited thereto. The parenteral administration route includes, for example, transdermal, intranasal, intraperitoneal, intramuscular, subcutaneous or intravenous routes.

Also, the pharmaceutical composition of the present disclosure may be administered in combination with a compound known to have an effect of preventing, remedying and/or treating climacteric disorder.

In another aspect, the present disclosure provides a food composition containing one of the compositions described above.

The food composition of the present disclosure includes all types of processed forms such as food, functional food, nutritional supplement, health food, food additive, etc. The food composition may be prepared into various forms according to a common method known in the art.

For example, the health food may be taken in after being prepared into a tea, a juice, a drink, a granule, a capsule or a powder. In addition, the food composition of the present disclosure may further contain another active ingredient and/or additive that can be commonly contained in a food composition in the art.

For example, the food composition according to the present disclosure may contain a water-soluble vitamin such as thiamine (vitamin $B_1$), riboflavin, ascorbic acid, niacin and vitamin $B_6$, a fatty acid such as myristic acid, palmitic acid, stearic acid, oleic acid, linoleic acid, etc., a weak acid such as glycolic acid and acetic acid, and amino acids including 8 essential amino acids, threonine, valine, methionine, isoleucine, leucine, phenylalanine, tryptophan and lysine, aspartic acid, serine, glutamic acid, proline, glycine, alanine, cysteine, tyrosine, histidine, arginine, etc.

In another aspect, the present disclosure provides a cosmetic composition containing one of the compositions described above.

The cosmetic composition of the present disclosure may contain, in addition to the active ingredient of the present disclosure, ingredients commonly used in a cosmetic composition, for example, a common adjuvant such as an antioxidant, a stabilizer, a solubilizer, a vitamin, a pigment and a flavor, and a carrier.

The cosmetic composition according to the present disclosure may be prepared into any formulation commonly used in the art. For example, it may be formulated into a solution, a suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto.

More specifically, it may be formulated into a softening lotion, a nourishing lotion, a nourishing cream, a massage cream, an essence, an eye cream, a cleansing cream, a cleansing foam, a cleansing water, a pack, a spray or a powder.

When the formulation of the present disclosure is a solution or an emulsion, a solvent, a solubilizer or an emulsifier may be used as a carrier. For example, water, ethanol, isopropanol, ethyl carbonate, ethyl acetate, benzyl alcohol, benzyl benzoate, propylene glycol, 1,3-butylene glycol, glycerol aliphatic ester, polyethylene glycol or sorbitan fatty acid ester may be used.

When the formulation of the present disclosure is a suspension, a liquid diluent such as water, ethanol or propylene glycol, a suspending agent such as ethoxylated isostearyl alcohol, polyoxyethylene sorbitol ester or polyoxyethylene sorbitan ester, microcrystalline cellulose, aluminum metahydroxide, bentonite, agar, tragacanth, etc. may be used as a carrier.

When the formulation of the present disclosure is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives, ethoxylated glycerol fatty acid ester, etc. may be used as a carrier.

When the formulation of the present disclosure is a powder or a spray, lactose, talc, silica, aluminum hydroxide, calcium silicate or polyamide powder may be used as a carrier. In particular, when it is a spray, a propellant such as chlorofluorohydrocarbon, propane/butane or dimethyl ether may be further contained.

When the formulation of the present disclosure is a paste, a cream or a gel, animal oil, plant oil, wax, paraffin, starch, tragacanth, cellulose derivatives, polyethylene glycol, silicone, bentonite, silica, talc, zinc oxide, etc. may be used as a carrier.

Advantageous Effects

Because a composition according to the present disclosure shows quick effects for preventing, remedying and/or treating female climacteric syndrome symptoms, particularly facial flushing and/or osteoporosis, it can be utilized for the hormone replacement therapy (HRT) used for preventing or remedying climacteric syndrome symptoms.

In addition, because the composition according to the present disclosure has no cytotoxicity unlike existing therapeutic agents for female climacteric syndrome symptoms, particularly sweating, facial flushing or osteoporosis, and is safe with few side effects as much as it can be used as food, it can be utilized as a therapeutic agent for female climacteric syndrome symptoms, particularly sweating, facial flushing or osteoporosis.

BEST MODE

Hereinafter, the present disclosure is described in detail through examples and test examples. However, the examples and test examples according to the present disclosure may be changed into various other forms, and it should not be construed that the scope of the present disclosure is limited to the examples and test examples. The examples and test examples of the present disclosure are provided to describe the present disclosure more completely to those of ordinary skill in the art.

Comparative Analysis of Plants in Genus *Pueraria*

Example 1. Preparation of *Pueraria thomsonii* and *Pueraria lobata* Extracts

*Pueraria thomsonii* and *Pueraria lobata* were used in the following examples. The plants in the genus *Pueraria* were extracted at 70° C. for 4 hours with 85% ethanol as a solvent and then concentrated under reduced pressure to prepare each extract.

Example 2. Preparation of Tablet 300-mg tablets described in Table 1 were prepared using the *P. thomsonii* extract and the *P. lobata* extract prepared in Example 1 and an excipient (dextrin) as the balance.

TABLE 1

| | Composition (%) | | |
|---|---|---|---|
| | *P. thomsonii* extract | *P. lobata* extract | Dextrin |
| Preparation Example 1 | — | — | 100 |
| Preparation Example 2 | 30 | — | Balance |
| Preparation Example 3 | — | 30 | Balance |

Example 3. Evaluation of Activity for Estrogen Receptors

ERE (estrogen response element) reporter assay was performed to investigate the activity of the *P. thomsonii* extract and the *P. lobata* extract for estrogen receptors.

Figure 1:
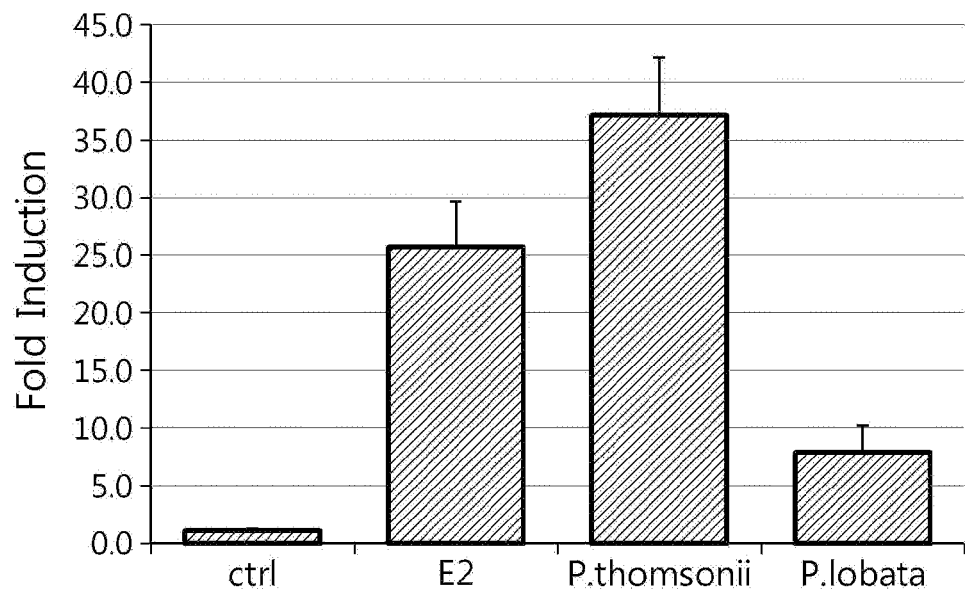
FIG. 1 is a graph showing the activity of a *P. thomsonii* extract and a *P. lobata* extract according to an exemplary embodiment of the present disclosure for estrogen receptors.

After culturing 293T cells using a DMEM medium supplemented with 10% FBS in a 24-well plate for 24 hours, the medium was replaced with 500 µL of a 5% charcoal-stripped FBS containing phenol red-free medium per well and then transfection was carried out. DNA transfection was carried out using the Lipofectamine® reagent (Thermo Fisher Scientific) (0.1 µg of ERa, 0.1 µg of ERE and 10 ng of pRL-Tk) per well. After conducting the transfection for 4 hours, 10 ppm (DMSO 0.5 µL) of the *P. thomsonii* extract or the *P. lobata* extract was added. For a positive control group, 1 ppb (DMSO 0.5 µL) of 17β-estradiol (E2) was treated. For a negative control group (control, ctrl), DMSO of the same volume (0.5 µL) was treated. 24 hours after the treatment, luminescence was measured using the Dual-Luciferase® reporter assay system (Promega), and the experimental result is shown in FIG. 1 relative to the measurement value for the negative control group (1.0). The measurement value for firefly luciferase was corrected with the value for renilla luciferase.

As shown in FIG. 1, the *P. thomsonii* extract showed better activity for estrogen receptors than the *P. lobata* extract.

Figure 2:
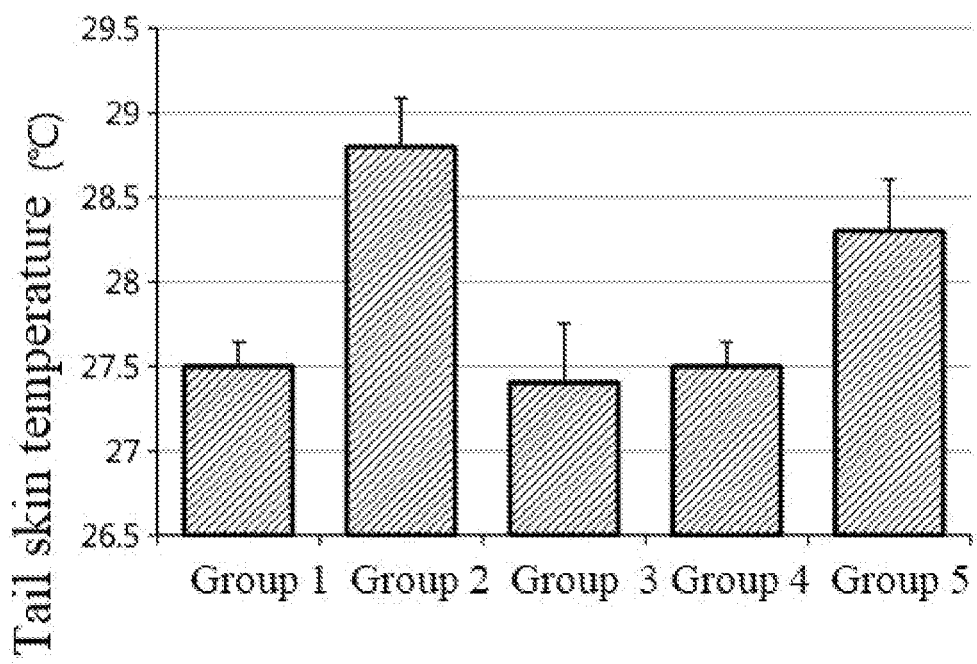
FIG. 2 is a graph showing the effect of remedying a vasomotor symptom of a *P. thomsonii* extract and a *P. lobata* extract according to an exemplary embodiment of the present disclosure.

Example 4. Activity of *P. thomsonii* Extract Depending on Solvent (Ethanol:Water) Composition After extracting dried *Pueraria thomsonii* at 70° C. for 4 hours using the solvents (ethanol:water) described in Table 2, an extract was prepared by concentrating under reduced pressure. ERE (estrogen response element) reporter assay was conducted to investigate the activity for estrogen receptors. The experiment was conducted in the same manner as in Example 3, and each extract was added at 10 ppm. The experimental result is shown in FIG. 2 relative to the measurement value for the negative control group (1.0).

As shown in Table 2, the activity for estrogen receptors was superior for 35-95% ethanol solvents, and the most superior activity was achieved for 60-90% ethanol solvents.

TABLE 2

| Ethanol:water ratio | Fold induction |
|---|---|
| 95:5 | 27.4 |
| 85:15 | 35.7 |
| 75:25 | 31.1 |
| 65:35 | 33.4 |
| 55:45 | 28.7 |
| 45:55 | 27.1 |
| 35:65 | 28.6 |
| 25:75 | 18.9 |
| 10:90 | 14.2 |
| 100:0 | 12.9 |

Example 5. Effect of Relieving Climacteric Syndrome Symptoms of *P. thomsonii* Extract 60 women in their late 40s to 50s suffering from climacteric syndrome symptoms were divided randomly and were asked to take in the tablets prepared in Preparation Examples 1-3, 3 tablets a day. The degree of remedying climacteric syndrome symptoms was evaluated 2 weeks and 4 weeks after the intake.

2 weeks and 4 weeks after the intake, the degree of remedying climacteric syndrome symptoms was measured with a Kupperman index. The decrease (%) of the Kupperman index as compared to before the intake is shown in Table 3.

The Kupperman index (KI) used in the present disclosure is a menopause index which rates the 11 symptoms occurring in postmenstrual women (facial flushing, sweating, insomnia, nervousness, depression, dizziness, fatigue, arthralgia, muscular pain, headache, palpitation, vaginal dryness). The menopausal score is calculated by multiplying each score by a weight and then summing them.

TABLE 3

| | Preparation Example 1 | | Preparation Example 2 | | Preparation Example 3 | |
|---|---|---|---|---|---|---|
| | 2 weeks | 4 weeks | 2 weeks | 4 weeks | 2 weeks | 4 weeks |
| Decrease of Kupperman index (%) | 2.3 | 5.3 | 17.6 | 32.0 | 7.5 | 16 |

As shown in Table 3, the composition of Preparation Example 2 in which the *P. thomsonii* extract was mixed showed excellent effect of relieving climacteric syndrome symptoms as compared to the placebo group of Preparation Example 1 or the composition of Preparation Example 3 in which the *P. lobata* extract was mixed.

In particular, the decrease in 'facial flushing' among the climacteric syndrome symptoms was investigated. As shown in Table 4, Preparation Example 2 showed the largest increase.

From the result of Table 4, it can be seen that the *P. thomsonii* extract of the present disclosure has superior effect of decreasing and treating facial flushing.

TABLE 4

| | Preparation Example 1 | | Preparation Example 2 | | Preparation Example 3 | |
|---|---|---|---|---|---|---|
| | 2 weeks | 4 weeks | 2 weeks | 4 weeks | 2 weeks | 4 weeks |
| Decrease of facial flushing (%) | 5 | 7 | 15 | 30 | 7 | 12 |

Example 6. Effect of Remedying Vasomotor Symptoms

It is known that 75% of postmenstrual women experience vasomotor symptoms. Facial flushing (hot flush) is the representative symptom where the skin on face, neck and chest is reddened abruptly, accompanied by unpleasant flushing and sweating. The change in the vasomotor symptoms can be evaluated by measuring the change in skin temperature. In an animal experiment, it can be measured by the skin temperature of the rat tail (Guidelines for evaluation of health functional food, 'Helpful for health of postmenstrual women', National Institute of Food and Drug Safety Evaluation).

11-12 week-old female Sprague-Dawley rats were subjected to sham operation (group 1, n=10) or ovariectomy (OVX) (groups 2-5, n=10 per each group). After a week from the operation, 0.01 mL of a sample per body weight (g) of each rat was administered orally every day for 4 weeks. 17β-Estradiol (E2) was administered to the positive control group and the *P. thomsonii* extract or the *P. lobata* extract was administered to the test groups. 4 weeks after the administration, the skin temperature at 2 cm where the tail starts was measured using an infrared thermometer. The measurement result is shown in FIG. 2.

TABLE 5

| Group | Operation | Sample |
|---|---|---|
| Group 1 | Sham | Drinking water |
| Group 2 | OVX | Drinking water |
| Group 3 | OVX | 17β-Estradiol (E2), 0.5 mg/kg/day |
| Group 4 | OVX | *P. thomsonii* extract, 100 mg/kg/day |
| Group 5 | OVX | *P. lobata* extract, 100 mg/kg/day |

As seen from FIG. 2, the group to which the *P. thomsonii* extract was administered showed suppressed increase in the tail temperature caused by estrogen deficiency.

Example 7. Effect of Remedying Bone Resorption

In order to measure CTX (C-terminal telopeptide of type I collagen), which is a marker related with bone resorption, the same rats as in Example 6 were orally administered with a sample for 8 weeks and then serum was collected. The CTX level in the serum was measured using the rat C-telopeptide of type I collagen ELISA kit (MyBioSource) according to the manufacturer's instructions. The result is shown in FIG. 3.

Figure 3:
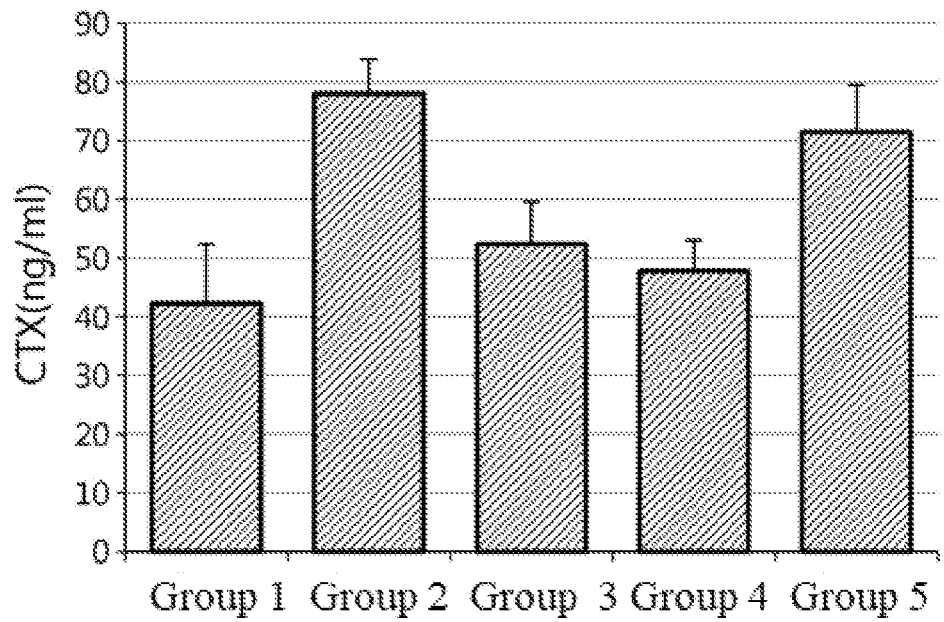
FIG. 3 is a graph showing the effect of remedying bone resorption of a *P. thomsonii* extract and a *P. lobata* extract according to an exemplary embodiment of the present disclosure.

As seen from FIG. 3, the group to which the *P. thomsonii* extract was administered showed significantly decreased CTX level as compared to the OVX group, suggesting that bone resorption was decreased.

It was confirmed that the activity for estrogen receptors of the *P. thomsonii* extract was excellent as compared to the activity for estrogen receptors of the *P. lobata* extract (Example 3).

It was confirmed that the *P. thomsonii* extract also had superior effect of relieving female climacteric syndrome symptoms (Example 5, Example 6 and Example 7).

Accordingly, the *Pueraria thomsonii* extract exhibiting superior activity for estrogen receptors can be used effectively for preventing, treating or remedying female climacteric syndrome symptoms, particularly facial flushing or osteoporosis.

Comparative Analysis of Different Parts of *Pueraria thomsonii*

Example 8. Preparation of Extracts of Different Parts of *Pueraria thomsonii*

After harvesting, drying and pulverizing the bud, root and leaf of *Pueraria thomsonii*, extracts were prepared by extracting 70° C. for 4 hours with 85% ethanol as a solvent and then concentrating under reduced pressure.

Example 9. Preparation of Tablet 300-mg tablets described in Table 6 were prepared using the extracts of the different parts of *P. thomsonii* and an excipient (dextrin) as the balance.

TABLE 6

| | Composition (%) | | | |
|---|---|---|---|---|
| | Bud | Root | Leaf | Dextrin |
| Preparation Example 4 | | | | 100 |
| Preparation Example 5 | 30 | | | 70 |
| Preparation Example 6 | | 30 | | 70 |
| Preparation Example 7 | | | 30 | 70 |

Example 10. Effect of Relieving Climacteric Syndrome Symptoms of Extracts of Different Parts of *P. thomsonii*

60 women in their late 40s to 50s suffering from climacteric syndrome symptoms were divided randomly and were asked to take in the tablets prepared in Preparation Examples 4-7, 3 tablets a day. The degree of remedying climacteric syndrome symptoms was evaluated 2 weeks and 4 weeks after the intake.

2 weeks and 4 weeks after the intake, the degree of remedying climacteric syndrome symptoms was measured with a Kupperman index. The decrease (%) of the Kupperman index as compared to before the intake is shown in Table 7.

The Kupperman index (KI) used in the present disclosure is a menopause index which rates the 11 symptoms occurring in postmenstrual women (facial flushing, sweating, insomnia, nervousness, depression, dizziness, fatigue, arthralgia, muscular pain, headache, palpitation, vaginal dryness). The menopausal score is calculated by multiplying each score by a weight and then summing them.

TABLE 7

| | Preparation Example 4 | | Preparation Example 5 | | Preparation Example 6 | | Preparation Example 7 | |
|---|---|---|---|---|---|---|---|---|
| | 2 weeks | 4 weeks | 2 weeks | 4 weeks | 2 weeks | 4 weeks | 2 weeks | 4 weeks |
| Decrease of Kupperman index (%) | 3.5 | 7.8 | 18.5 | 33.9 | 9.4 | 20.0 | 5.4 | 10.7 |

As shown in Table 7, the composition of Preparation Example 5 in which the bud extract was mixed showed excellent effect of relieving climacteric syndrome symptoms as compared to Preparation Example 4 (placebo group) or Preparation Example 6 and Preparation Example 7 in which the root or leaf extract was mixed.

In particular, the decrease in 'facial flushing' among the climacteric syndrome symptoms was investigated. As shown in Table 8, Preparation Example 5 showed the largest increase.

From the result of Table 8, it can be seen that the *P. thomsonii* bud extract of the present disclosure has superior effect of decreasing and treating facial flushing.

TABLE 8

| | Preparation Example 4 | | Preparation Example 5 | | Preparation Example 6 | | Preparation Example 7 | |
|---|---|---|---|---|---|---|---|---|
| | 2 weeks | 4 weeks | 2 weeks | 4 weeks | 2 weeks | 4 weeks | 2 weeks | 4 weeks |
| Decrease of facial flushing (%) | 3.8 | 8.8 | 18.0 | 32.8 | 9.7 | 14.6 | 8.7 | 12.8 |

Example 11. Effect of Remedying Vasomotor Symptoms

It is known that 75% of postmenstrual women experience vasomotor symptoms. Facial flushing (hot flush) is the representative symptom where the skin on face, neck and chest is reddened abruptly, accompanied by unpleasant flushing and sweating. The change in the vasomotor symptoms can be evaluated by measuring the change in skin temperature. In an animal experiment, it can be measure by the skin temperature of the rat tail (Guidelines for evaluation of health functional food, 'Helpful for health of postmenstrual women', National Institute of Food and Drug Safety Evaluation).

11-12 week-old female Sprague-Dawley rats were subjected to sham operation (group 1, n=10) or ovariectomy (OVX) (groups 2-6, n=10 per each group). After a week from the operation, 0.01 mL of a sample per body weight (g) of each rat was administered orally every day for 4 weeks. 17β-Estradiol (E2) was administered to the positive control group and the extracts of different parts of *P. thomsonii* were administered to the test groups. 4 weeks after the administration, the skin temperature at 2 cm where the tail starts was measured using an infrared thermometer. The measurement result is shown in FIG. 4.

TABLE 9

| Group | Operation | Sample |
| --- | --- | --- |
| Group 1 | Sham | Drinking water |
| Group 2 | OVX | Drinking water |
| Group 3 | OVX | 17β-Estradiol (E2), 0.5 mg/kg/day |
| Group 4 | OVX | *P. thomsonii* bud extract, 100 mg/kg/day |
| Group 5 | OVX | *P. thomsonii* root extract, 100 mg/kg/day |
| Group 6 | OVX | *P. thomsonii* leaf extract, 100 mg/kg/day |

Figure 4:
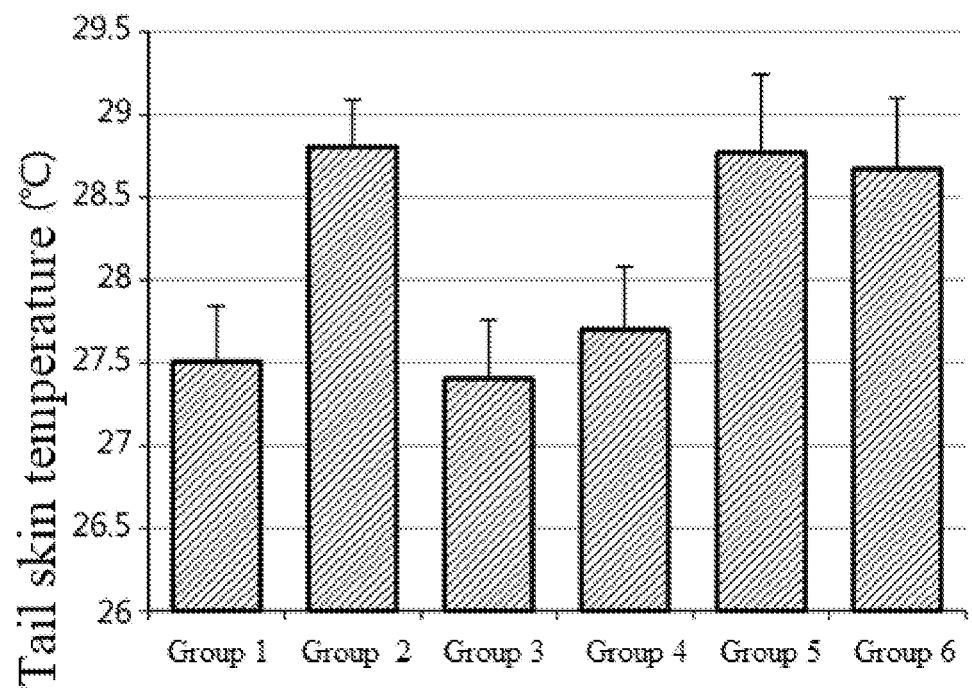
FIG. 4 is a graph showing the effect of remedying a vasomotor symptom of extracts of different parts of *P. thomsonii* according to an exemplary embodiment of the present disclosure.

As seen from FIG. 4, the group to which the *P. thomsonii* bud extract was administered showed suppressed increase in the tail temperature caused by estrogen deficiency.

Example 12. Effect of Remedying Bone Resorption

In order to measure CTX (C-terminal telopeptide of type I collagen), which is a marker related with bone resorption, the same rats as in Example 8 were orally administered with a sample for 8 weeks and then serum was collected. The CTX level in the serum was measured using the rat C-telopeptide of type I collagen ELISA kit (MyBioSource) according to the manufacturer's instructions. The result is shown in FIG. 5.

Figure 5:
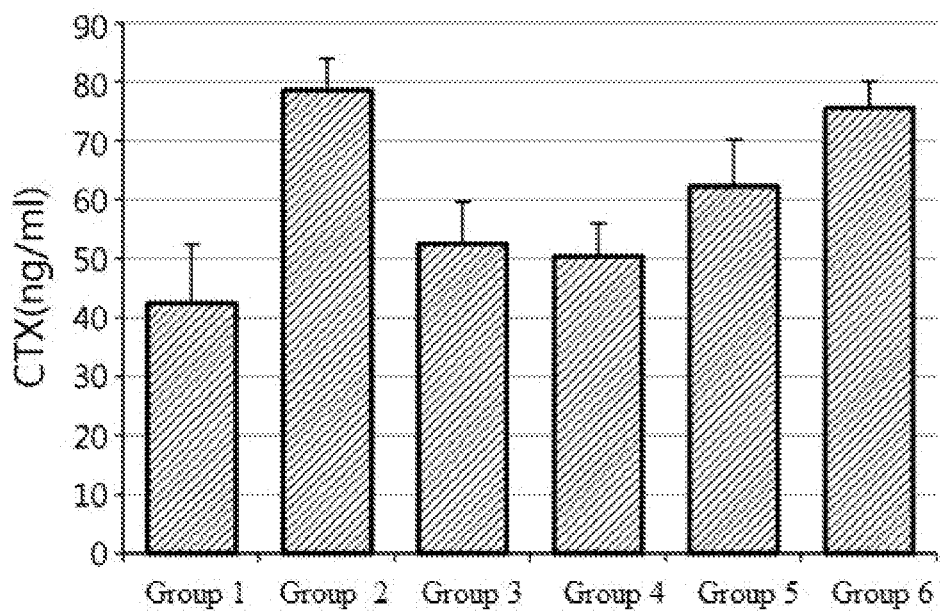
FIG. 5 is a graph showing the effect of remedying bone resorption of extracts of different parts of *P. thomsonii* according to an exemplary embodiment of the present disclosure.

As seen from FIG. 5, the group to which the *P. thomsonii* bud extract was administered showed significantly decreased CTX level as compared to the OVX group, suggesting that bone resorption was decreased.

INDUSTRIAL APPLICABILITY

The present disclosure provides a pharmaceutical composition and/or a food composition which is effective for preventing or remedying female climacteric syndrome symptoms and/or sweating, facial flushing or osteoporosis.

It can be utilized for the hormone replacement therapy (HRT) used for preventing or remedying climacteric syndrome symptoms.

In addition, because the composition according to the present disclosure has no cytotoxicity unlike existing therapeutic agents for female climacteric syndrome symptoms, particularly sweating, facial flushing or osteoporosis, and is safe with few side effects as much as it can be used as food, it can be utilized as a therapeutic agent for female climacteric syndrome symptoms, particularly sweating, facial flushing or osteoporosis.

What is claimed is:

1. A method for treating or remedying female climacteric syndrome symptoms by administering to a subject in need thereof a therapeutically effective amount of a composition comprising an extract of buds of *Pueraria thomsonii*.

2. The method according to claim 1, wherein the *Pueraria thomsonii* bud extract is an ethanol extract.

3. The method according to claim 2, wherein the ethanol extract extract is a 60-90% ethanol extract.

4. The method according to claim 1, wherein the female climacteric syndrome symptom is facial flushing.

5. The method according to claim 1, wherein the female climacteric syndrome symptom is osteoporosis.

6. The method according to claim 1, wherein the female climacteric syndrome symptom is sweating.

* * * * *